US006824988B2

(12) United States Patent
Roelens et al.

(10) Patent No.: US 6,824,988 B2
(45) Date of Patent: Nov. 30, 2004

(54) METHOD AND COMPOSITIONS FOR USE IN DIAGNOSING AND CHARACTERIZING CHRONIC IMMUNE DISEASE

(75) Inventors: Simon Adriaan Michiel Roelens, Kortrijk (BE); Patrick Englebienne, Zingem (BE); Anne Marie Yvonne Robert D'Haese, Pinte (BE); C. V. Taylor Herst, Oakland, CA (US)

(73) Assignee: R.E.D. Laboratories, N.V., Zellik (BE)

( * ) Notice: Subject to any disclaimer, the term of this patent is extended or adjusted under 35 U.S.C. 154(b) by 0 days.

(21) Appl. No.: 09/571,582

(22) Filed: May 15, 2000

(65) Prior Publication Data

US 2003/0152919 A1 Aug. 14, 2003

(51) Int. Cl.$^7$ ................................................ C12O 1/68
(52) U.S. Cl. ............................ 435/7.1; 435/6; 435/7.1; 435/7.4; 435/7.92; 435/18; 435/21; 435/22; 435/23; 435/24; 435/4; 436/515; 436/516; 436/63; 530/350; 536/28.1
(58) Field of Search ......................... 435/6, 7.4, 7.92, 435/18, 21, 23, 24, 4, 975, 7.1, 7.21–7.24; 530/350; 536/28.1; 436/515, 516, 63

(56) References Cited

U.S. PATENT DOCUMENTS

| | | | |
|---|---|---|---|
| 4,444,879 A | * | 4/1984 | Foster et al. .................. 435/7.1 |
| 5,240,834 A | * | 8/1993 | Frankel et al. ............. 435/71.2 |
| 5,766,859 A | | 6/1998 | Vojdani et al. .............. 435/7.1 |
| 5,776,690 A | | 7/1998 | Vojdani et al. ............. 435/91.2 |
| 5,830,668 A | | 11/1998 | Mordechai et al. .......... 435/7.4 |
| 5,853,996 A | | 12/1998 | Mordechai et al. ............ 435/6 |
| 5,985,565 A | * | 11/1999 | Suhadolnik .................... 435/6 |
| 6,080,554 A | * | 6/2000 | Campine et al. .............. 435/21 |
| 6,214,554 B1 | * | 4/2001 | Suhadolnik .................... 435/6 |

FOREIGN PATENT DOCUMENTS

WO  WO 91/00097  1/1991

OTHER PUBLICATIONS

Komaroff (2000). "The biology of Chronic Fatigue Syndrome" *Am. J. Med.*, 108: 169–171.

Mashima et al. (1997). "Actin cleavage by CPP–32/apopain during the development of apoptosis" *Oncogene*, vol. 14: 1007–1012.

Mashima et al. (1999). "Caspase–mediated cleavage of cytoskeletal actin plays a positive role in the process of morphological apoptosis" *Oncogene*, vol. 18: 2423–2430.

Meirleir et al. (2000). "A 37kDa 2–5A Binding Protein as a Potential Biochemical Marker for Chronic Fatigue Syndrome" *Am. J. Med.*, vol. 108: 99–106.

Villa et al. (1998). "Calpain inhibitors, but not caspase inhibitors, prevent actin proceolysis and DNA fragmentation during apoptosis" *J. Cell Sci.*, vol. 111(Pt 6): 713–722.

(List continued on next page.)

*Primary Examiner*—Christopher L. Chin
*Assistant Examiner*—Gailene R. Gabel
(74) *Attorney, Agent, or Firm*—Bret E. Field; Bozicevic, Field & Francis

(57) ABSTRACT

Methods are provided for diagnosing and/or characterizing chronic immune disease activity in a subject. In the subject methods, a sample is obtained from a subject suspected of having or known to have a chronic immune disease. The sample is then assayed for the presence of low molecular actin fragments. The assay results are used to diagnose the presence of chronic immune disease activity and/or characterize chronic immune disease activity in the subject, e.g. to confirm an initial chronic immune disease diagnosis, to determine the stage of the disease, to monitor disease progression, to predict disease attacks, and the like. Also provided by the subject invention are kits for practicing the methods.

15 Claims, 3 Drawing Sheets

Detection of Actin and Actin Fragments by Western Blot. Lanes 1 – 13: Representative collection of cytoplasmic cell extracts from CFS patients and healthy controls. Lane 14: G-actin as control. The quantification by densitometry of (30 kDa/42kDa)*10 as compared to the value of RNase L species (LMW/HMW)*10, is provided in Table 1.

OTHER PUBLICATIONS

R. Suhadolnik et al. "Changes in the 2–5A synthetase/Rnase L Antiviral pathway in a controlled clinical trial with poly(l)–Poly($C_{12}$U) in chronic fatigue syndrome" In vivo 8:599–604 (1994).

R. Suhadolnik et al., "Biochemical evidence for a novel low molecular weight 2–5A–dependent Rnase L in chronic fatigue syndrome" *Journal of Interference and Cytokine Research* 17:377–385 (1997).

* cited by examiner

Detection of Actin and Actin Fragments by Western Blot. Lanes 1 – 13: Representative collection of cytoplasmic cell extracts from CFS patients and healthy controls. Lane 14: G-actin as control. The quantification by densitometry of (30 kDa/42kDa)*10 as compared to the value of RNase L species (LMW/HMW)*10, is provided in Table 1.

Correlation Between the Ratio of RNase L Fragments [Log10((LMW/HMW)*10)] and the Ratio of Actin Fragments [(LMW/HMW)*10] as Assayed in PBMC Extracts. Data points taken from Table 1.

Correlation Between the Relative Amount of Native RNase L Protein (80 kDa) in PBMC Extracts and the Relative Amount of Native Actin Protein (42 kDa) in Serum. Data points taken from Table 2.

US 6,824,988 B2

METHOD AND COMPOSITIONS FOR USE IN DIAGNOSING AND CHARACTERIZING CHRONIC IMMUNE DISEASE

TECHNICAL FIELD

The field of this invention is chronic immune disease, particularly chronic fatigue syndrome and multiple sclerosis.

BACKGROUND OF THE INVENTION

Chronic immune diseases can be highly debilitating. Two such chronic immune diseases are multiple sclerosis and chronic fatigue syndrome.

Multiple sclerosis (MS) is a neurological illness of unknown etiology associated with attacks of focal or multifocal neurological dysfunction arising from lesions within the central nervous system (CNS). In America and Northern Europe, MS is the most common neurological disease, with prevalence rates estimated between 50–100 per 100,000 population. The onset of disease is most common in early adulthood. Recurrent attacks can occur over many years, with approximately 30 percent of the patients progressing to a severe form of the disease which can be fatal.

MS is pleomorphic in its presentation. The clinical manifestations are determined in part by the location of the foci of demyelination within the CNS. Classical features of the disease include impaired vision, nystagmus, dysarthria, ataxia and intention tremor, and weakness/paralysis of one or more limbs.

The most common form of the disease is episodic. Symptoms develop with subsequent recovery, then another attack occurs. In approximately 50 percent of all patients with MS, attacks become more frequent, usually with a worsening of symptomatology. In 30 percent of all patients, the disease develops into what is referred to as progressive/relapsing, the most severe form of the disease. In this state remissions are rare and patients frequently become wheelchair bound.

The characterization of MS disease activity (including diagnosis, determination of disease state, monitoring of disease progression, prediction of disease attacks, and the like), remains problematic. To aid the clinician, the only laboratory test available is testing the cerebrospinal fluid for oligoclonal bands, present in approximately 90 percent of all patients. Examination of the brain for demyelinating plaques, using magnetic resonance imaging (MRI) is useful but expensive, and is not warranted except in a small group of patients in which all other clinical and laboratory tests are negative. Furthermore, there is no diagnostic laboratory test to determine if a patient is having an "attack," to monitor the progress of the "attack," to determine if the patient is progressing to a more active form of the disease (i.e., progressive/relapsing), etc. Finally, there is no laboratory test available as a prognostic indicator and/or capable of monitoring the course of therapy. One commentator has summarized the situation as follows: "The need for reliable markers of disease activity in multiple sclerosis (MS) to better guide basic research, diagnosis, treatment, and monitoring therapy is well-recognized." Laman et al., Mult. Scler. (Jun. 1998) 4:266–269.

Like MS, chronic fatigue syndrome (CFS) is an illness of unknown etiology. CFS is often associated with sudden onset, flu-like symptoms, debilitating fatigue, low-grade fever, myalgia and neurocognitive dysfunction. CFS patients typically display reduced Karnofsky performance scores (KPS). The Karnofsky performance test measures an individual's ability to function and carry on normal activities. Karnofsky scores range form zero for a nonfunctional or dead patient to 100 for a completely normal function.

Diagnosis of CFS remains one of exclusion. An accumulating body of evidence suggests that CFS is associated with disregulation of both humoral and cellular immunity, including mitogen response, reactivation of viruses, abnormal cytokine production, diminished natural killer cell function and changes in intermediary metabolites. It has been suggested that the clinical and immunological abnormalities observed in CFS might include defects in the double-stranded RNA (dsRNA)-dependent, interferon-inducible pathways, i.e., the 2',5'-oligoadenylate (2–5A) synthetase/RNase L and p68 kinase (PKR) antiviral defense pathways (Suhadolnik et al., Clin. Infect. Dis. (1994) 18:S96–S104; Suhadolnik et al., In Vivo (1994 8:599–604. The 2–5A synthetase/RNase L pathway is part of the antiviral defense mechanism in mammalian cells; this pathway also has a role in the regulation of cell growth and differentiation (Lengyel, Ann. Review Biochem. (1982) 51:251–282; Sen et al., Adv. Virus Res. (1993) 42:57–102).

When activated by dsRNA, 2–5A synthetase converts ATP to 2',5'-linked oligoadenylates with 5'-terminal phosphates. Biologically active 2–5A binds to and activates a latent endoribonuclease, RNase L, which hydrolyzes single-stranded viral and cellular RNA, primarily after UpNp sequences, thereby inhibiting protein synthesis.

Previous studies on the 2–5A synthetase/RNase L pathway in CFS revealed a statistically significant dysregulation in which the 2–5A synthetase is present predominantly in its activated form, bioactive 2–5A levels are elevated, and RNase L activity is upregulated (Suhadolnik et al., Clin. Infect. Dis., supra; Suhadolnik et al., In Vivo, supra). Expression of the serine-threonine kinase, PKR, is down-regulated in CFS (Suhadolnik et al., In Vivo, supra). PKR controls initiation of protein translation through phosphorylation of eIF-2.

Despite these efforts, a clear cut molecular marker for CFS has not been identified. What is needed is a biochemical test, relying on an unambiguous molecular marker for CFS, which may form the basis of a definitive CFS diagnosis.

As the above discussion demonstrates, currently employed methods of diagnosing and/or characterizing MS or CFS disease activity in a subject are inadequate. As such, there is a continued need in the field to develop additional means for diagnosing and/or characterizing MS or CFS disease activity in a subject.

3. Relevant Literature

U.S. Pat. Nos. of interest include:5,766,859; 5,776,690; 5,830,668; 5,853,996; and 5,985,565. Other references of interest include: De Meirlier et al., Am. J. Med. (2000) 108:99–105; Komaroff, Am. J. Med. (2000) 108:69–171; Mashima et al., Oncogene (1999) 18:2423–2430; Mashima et al., Oncogene (1997) 14: 1007–1012; and Villa et al., J. Cell. Sci. (1998) 111: 713–722.

SUMMARY OF THE INVENTION

Methods are provided for diagnosing and/or characterizing chronic immune disease activity in a subject. In the subject methods, a sample is obtained from a subject suspected of having or known to have a chronic immune disease. The sample is then assayed for the presence of low molecular weight actin fragments. The assay results are used to diagnose the presence of chronic immune disease activity and/or characterize chronic immune disease activity in the subject, e.g. to confirm an initial chronic immune disease diagnosis, to determine the stage of the disease, to monitor disease progression, to predict disease attacks, and the like. Also provided by the subject invention are kits for practicing the methods.

DESCRIPTION OF THE SPECIFIC EMBODIMENTS

Figure 1:
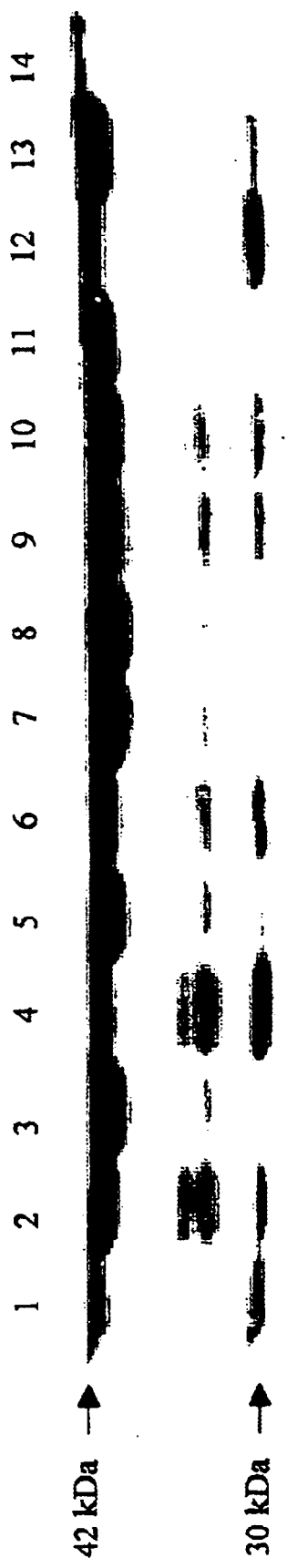
FIG. 1 represents a densitometric scan of a Western blot detecting actin protein and actin protein fragments. Native G-actin is clearly visible at 42 kDa as are the fragments (the 30 kDa fragment is indicated with an arrow).

Methods are provided for diagnosing and/or characterizing chronic immune disease activity in a subject. In the subject methods, a sample is obtained from a subject suspected of having or known to have a chronic immune disease. The sample is then assayed for the presence of low molecular weight actin fragments. The assay results are used to diagnose the presence of chronic immune disease activity and/or characterize chronic immune disease activity in the subject, e.g. to confirm an initial chronic immune disease diagnosis, to determine the stage of the disease, to monitor disease progression, to predict disease attacks, and the like. Also provided by the subject invention are kits for practicing the methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

As summarized above, the subject invention provides a method of diagnosing the presence of a chronic immune disease in a host. In other words, the subject invention provides a means for determining whether a host is suffering from a chronic immune disease. Specifically, the subject invention provides a method of determining whether a host is suffering from MS or CFS. MS and CFS are disease conditions as defined in the experimental section, supra.

In determining whether a host suffers from a chronic immune disease, a sample from the host is assayed for the presence of one or more low molecular weight fragments of actin. More specifically, a sample of the host is assayed for the presence of one or more low molecular weight fragments of G-actin. By low molecular weight actin fragment is meant a polypeptide that has a sequence of amino acid residues found in full length actin, where this sequence is at least about 10, usually at least about 20 and more usually at least about 50 residues long and is often longer, where the polypeptide has a molecular weight that is less than that molecular weight of full length actin, i.e. where the polypeptide has a molecular weight that is less than about 42 kDa, as measured by SDS-PAGE (see the experimental section, infra.) Specifically, the sample is assayed for low molecular weight actin fragments ranging in weight from about 12 to 37 kDa, usually from about 15 to 32 kDa and more usually from about 25 to 30 kDa. Of particular interest is the identification of actin fragments having the following molecular weights as determined by SDS-PAGE: 15 kDa and 30 kDa. Representative samples and assay methods for identifying the presence of, and amounts of, low molecular weight actin fragments are described in greater detail infra.

The presence (or absence) of the low molecular weight actin is then used to diagnose whether or not the host suffers from the chronic immune disease. In other words, the presence or absence of low molecular weight actin fragments in the sample is used to determine whether or not the host suffers from a chronic immune disease, such as CFS or MS. For example, in one embodiment, the presence of one or more low molecular weight actin fragments is used to determine whether the host suffers from CFS. Likewise, in another embodiment, the presence of one or more low molecular weight actin fragments is used to determine whether a host suffers from MS. As part of the diagnosis, one may also evaluate the subject for other symptoms of the disease of interest which is to be diagnosed, e.g. the MS or CFS symptoms described in the background section, supra, as well as in other parts of this application.

Also provided by the subject invention are methods of characterizing the chronic immune disease activity, e.g. CFS or MS disease activity, in a subject suspected of having, or known to have, a chronic immune disease, e.g. CFS or MS. Subjects suspected of having, or known to have, a chronic immune disease and thus amenable to the subject methods can be identified using any convenient protocol. One convenient protocol is diagnosis based on clinical symptoms. A number of different clinical symptoms may be used to identify subjects that may have or have the chronic immune disease of interest, where the specific symptoms employed will necessarily depend on the specific chronic immune disease. For example, where the chronic immune disease of interest is CFS, clinical symptoms of interest include: fatigue of six months or longer that causes a reduction in effort of greater than 50 percent of normal output, athralgia, myalgia, sore throat accompanied by swollen glands, cognitive dysfunction (e.g. memory loss); and the like. For MS, clinical symptoms include: weakness of the limbs; sensory symptoms, e.g. paresthesia or hypesthesia; ataxia; optic neuritis; diplopia; trigeminal neuralgia; facial paralysis; vertigo; urinary or bowel movement abnormalities; and cognitive dysfunction, e.g. memory loss, impaired attention, problem-solving difficulties, slowed information processing, and difficulty in shifting between cognitive tasks. The presence of one or more of the above symptoms may be used to identify subjects suspected of suffering from CFS or MS, respectively. Other assays may also be employed, including MRI imaging, the oligoclonal band assay described in greater detail infra, etc.

The first step of the subject methods is to obtain a suitable sample from the subject or patient of interest, i.e. a patient suspected of having or known to have the chronic immune disease of interest, e.g. CFS or MS. The sample is derived from any initial source that contains native actin and the low molecular weight actin fragments (if present). Sample sources of interest include, but are not limited to, many different physiological sources, e.g. CSF, urine, saliva, tears, tissue derived samples, e.g. homogenates, and blood or derivatives thereof.

In many embodiments, the sample is derived from cells that comprise the actin fragments of interest, if present—i.e. if the patient from which the cells are derived has chronic immune disease. In other embodiments, the sample may be derived from fluids into which the proteins of interest have been released, e.g. are present. In many embodiments, a suitable initial source for the patient sample is blood. As such, the sample employed in the subject assays of these embodiments is generally a blood derived sample. The blood derived sample may be derived from whole blood or a fraction thereof, e.g. serum, plasma, etc., where in many embodiments the sample is derived from blood cells harvested from whole blood. Of particular interest as a sample source are mononuclear cells. As such, a preferred sample is one that is derived from peripheral blood mononuclear cells (PBMCs). In certain situations, the sample may be treated to displace actin fragments from actin transport proteins, where any convenient treatment protocol may be employed, e.g. acidification, etc.

In these preferred embodiments in which the sample is a PBMC derived sample, the sample is generally a fluid PBMC derived sample. Any convenient methodology for producing a fluid PBMC sample may be employed. In many embodiments, the fluid PBMC derived sample is prepared by: (a) separating PBMCs from whole blood, i.e. collecting PBMCs, e.g. by centrifugation (such as by Ficoll-Hypaque density gradient centrifugation); (b) disrupting the collected cells, e.g. by contacting with a lysing buffer; (c) and removing the resultant cellular debris to obtain a cell-free extract, e.g. by centrifugation. A representative means for producing a suitable fluid PBMC derived sample, i.e. a fluid PBMC extract, is disclosed in WO 98/15646 and U.S. Pat. No. 5,985,565; the disclosures of which is herein incorporated by reference.

Once the patient derived sample is obtained, it is assayed for the presence or absence of one or more low molecular weight actin fragments, either directly or indirectly. The low molecular weight actin fragments of interest are those having a molecular weight ranging from about 12 to 37 kDa, usually from about 15 to 32 kDa and specifically of about 25 to 30 kDa, as determined under SDS-PAGE reducing conditions, as described above, with specific fragments of interest being those having the following molecular weights: 15 kDa and 30 kDa.

The sample may be assayed for the presence or absence of the low molecular weight actin fragments using any convenient methodology. In many embodiments, such methodology involves the following two steps: (a) fractionation of the sample in a manner sufficient such that the one or more actin fragments and the native actin (if present) are present in different fractions, i.e. separating the low molecular weight fragments from each other and from the native actin; and (b) detection of the low molecular weight fragments in the specific fractions, i.e. assaying each fraction for the presence or absence of an actin fragment, where the detection may be qualitative, semi-quantitative or quantitative, and is usually at least semi-quantitative (i.e. not just qualitative).

In these embodiments, fractionation may be accomplished using any convenient methodology. The fractionation technique employed may or may not employ native or non-denaturing conditions. Whether fractionation is carried out under denaturing or non-denaturing conditions depends on the particular manner in which the low molecular weight fragments are detected, e.g. whether or not a non-denatured form is required for detection, where representative detection methods are described in greater detail below. Typically, the non-denaturing conditions are "native" conditions. By "native conditions" is meant fractionation by a process that substantially preserves the conformation and folding of the low molecular fragment species in the sample. Native conditions are those conditions that do not denature proteins. A variety of non-denaturing fractionation means are known to those of skill in the art, where one means of interest is gel filtration high performance liquid chromatography. Alternatively, fractionation may be carried out under non-native, e.g. denaturing conditions, such as SDS-PAGE (sodium dodecylsulfate-polyacrylamide gel electrophoresis). As the fractionating step involves separating the various low molecular weight actin fragments, fractionation results in the production of one or more fractions that putatively contain the low molecular actin fragment (i.e. is suspected of containing a low molecular weight fragment).

As discussed above, the sample or fraction(s) thereof are assayed for the presence or absence of low molecular weight actin fragments, where the assay may be a direct assay or an indirect assay. By direct assay is meant an assay that provides for a direct detection of low molecular weight actin fragments, e.g., an assay yield direct information regarding the presence and often amount of low molecular weight actin fragments in sample, e.g. an assay where an actin specific antibody is employed to detect low molecular weight actin fragments in an appropriately fractionated sample. By indirect assay is meant an assay that detects the presence or absence of low molecular weight actin fragments through detection, usually quantitation, of another species, e.g. native actin and total actin species (e.g., where a relative amount of native actin to total actin species in a sample is determined, from which the presence of low molecular weight actin fragments is indirectly determined). As such, the assay employed may or may not also include a determination of the amount of native or full length actin, i.e. actin having a molecular weight of 42 kDa or higher, in the sample.

Any convenient assay protocol may be employed. Suitable assays that may be employed include antibody based assays, e.g. Western blot assays, such as those described in the experimental section infra. Antibody based assays require the use of antibodies specific for the actin fragments and native actin. The assays may be direct assays, i.e., those which employ antibodies specific for low molecular weight actin fragments. Alternatively, the assays may be indirect assays, i.e., those which detect native actin and total amounts of actin species in a sample, e.g., an assay in which an antibodies specific for the C- and N-termini of the native actin are employed.

Antibodies that specifically bind to the subject actin protein and low molecular weight fragments thereof can be prepared using a variety of convenient methods known to those of skill in the art. See Guide to Protein Purification, supra, as well as Antibodies, A Laboratory Manual (Harlow & Lane eds., Cold Spring Harbor Press)(1988). The antibodies may be polyclonal or monoclonal antibodies depending on the nature of the intended use, as long as they are specific for one or more forms of actin or fragments thereof of interest.

For preparation of polyclonal antibodies, the first step is immunization of the host animal with actin or an immunogenic fragment, including fragment derivative thereof, where the actin immunogen will preferably be in substantially pure form, comprising less than about 1% contaminant. The immunogen may comprise complete actin, fragments or derivatives thereof. To increase the immune response of the host animal, the immunogen may be combined with an adjuvant, where suitable adjuvants include alum, dextran, sulfate, large polymeric anions, oil & water emulsions, e.g. Freund's adjuvant, Freund's complete adjuvant, and the like. The immunogen may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The immunogen is administered to the host, usually intradermally, with an initial dosage followed by one or more, usually at least two, additional booster dosages. Following immunization, the blood from the host is collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for actin and fragments thereof is to immunize a suitable host, where suitable hosts include rats, hamsters, mice and the like, and are preferably mice. The actin immunogen, which as above, may be the entire actin protein or a fragment or derivative thereof, is administered to the host in any convenient manner, where such methods include: subcutaneous injection with adjuvants, nitrocellulose implants comprising the immunogen, intrasplenic injections, and the like, where the immunization protocol may be modulated to obtain a desired type of antibody, e.g. IgG or IgM, where such methods are known in the art. Following immunization, plasma cells are harvested from the immunized host, where sources of plasma cells include the spleen, lymph nodes and the like, with the spleen being preferred. The plasma cells are then immortalized with myeloma cells to produce hybridoma cells. A variety of myeloma cell lines are available and known to those of skill in the art. The plasma and myeloma cells are fused by combining the cells in a fusion medium usually in a ratio of about 10 plasma cells to 1 myeloma cell, where suitable fusion mediums include a fusion agent, e.g. PEG 1000, and the like. Following fusion, the fused cells are selected, e.g. by growing on HAT medium. Following hybridoma cell production, culture supernatant from individual hybridomas is screened for reactivity with actin using standard techniques, where such screening techniques include ELISA, dot blot immunoassays and the like. The antibody may be purified from the supernatants or ascites fluid by conventional techniques, e.g. affinity chromatography actin bound to an insoluble support, protein A sepharose and the like.

Antibodies specific for actin are known in the art, and include those deposited at the ATCC under the following accession nos.: 5483 RE; 5462 RE; 9190 RE; 9197 RE; 10406 RE; etc.

The above prepared or obtained antibodies may be modified in a number of different ways to optimize their utility for use in a particular immunoassay. For example, antibody fragments, such as Fv, F(ab')$_2$ and Fab may be prepared by cleavage of the intact protein, e.g. by protease or chemical cleavage.

The antibodies, fragments or derivatives thereof may also be labeled in order to facilitate detection. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as $^3$H or $^{125}$I, fluorescers, dyes, beads, chemilumninescers, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In immunoassays of the subject invention, a number of different immunoassay formats are known in the art and may be employed. Representative assay formats include Western blots on protein gels or protein spots on filters, where the antibody is labeled as described above, as is known in the art. For a representative example of a Western blot assay for the presence of actin and fragments thereof in a sample, see the experimental section infra.

Other immunoassays include those based on competitive formats, as are known in the art. One such format would be where a solid support is coated with actin. Labeled antibody is then combined with the patient derived sample suspected to produce a reaction mixture which, following sufficient incubation time for binding complexes to form, is contacted with the solid phase bound actin. The amount of labeled antibody which binds to the solid phase will be proportional to the amount of actin or fragments thereof in the sample, and the presence of actin and fragments thereof may therefore be detected. Other competitive formats that may be employed include those where the sample suspected of comprising actin fragments is combined with a known amount of labeled actin fragments and then contacted with a solid support coated with antibody specific for actin fragments. Such assay formats are known in the art and further described in both Guide to Protein Purification, supra, and Antibodies, A Laboratory Manual, supra. Sandwich-format assays may also be employed. A sandwich assay is performed by initially attaching a first of the two types of antibodies to an insoluble surface or support. This first antibody may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. The insoluble supports may be any compositions to which antibodies or fragments thereof can be bound, which is readily separated from soluble material, and which is otherwise compatible with the overall method of measuring actin in the sample. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples. Before adding patient samples or fractions thereof, the non-specific binding sites on the insoluble support i.e. those not occupied by the first antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used. Samples, fractions or aliquots thereof are then added to separately assayable supports (for example, separate wells of a microtiter plate) containing support-bound allergen. Preferably, a series of standards, containing known concentrations of RNAse L is assayed in parallel with the samples or aliquots thereof to serve as controls. Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for RNAse L molecules to bind the insoluble first antibody. Generally, from about 0.1 to 3 hr is sufficient, usually 1 hr sufficing. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample. After washing, a solution containing the second actin or actin fragment specific antibody is applied. The second antibody may be labeled, as described above, to facilitate direct, or indirect detection and/or quantification of binding. Examples of labels which permit direct measurement of immunocomplexes include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the second antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the antibody may be unlabeled. In this case, a labeled second receptor-specific compound is employed which binds to the second antibody. Such a second receptor-specific compound can be labeled in any of the above manners. It is possible to select such compounds such that multiple compounds bind each molecule of bound second receptor. Examples of second antibody/second receptor-specific molecule pairs include antibody/anti-antibody and avidin (or streptavidin)/biotin. Since the resultant signal is thus amplified, this technique may be advantageous where only a small amount of actin or fragment thereof is present. An example is the use of a labeled antibody specific to the second antibody. The volume, composition and concentration of second antibody solution provides for measurable binding to the actin already bound to the first antibody. Generally, the same volume as that of the sample is used: from about 0.001 to 1 ml is sufficient, usually about 0.1 ml sufficing. The concentration will generally be sufficient to saturate all actin potentially bound to first antibody. The concentration generally will be about 0.1 to 50 $\mu$g/ml, preferably about 1 $\mu$g/ml. The solution containing the second antibody is generally buffered in the range of about pH 6.5–9.5. The solution may also contain an innocuous protein as previously described. The incubation time should be sufficient for the labeled ligand to bind available molecules. Generally, from about 0.1 to 3 hr is sufficient, usually 1 hr sufficing. After the second antibody has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490–495 nm is conveniently measured with a spectrophotometer.

Depending on the particular nature of the antibody based assay employed, it may be desirable to employ antibodies that are capable of distinguishing between the various actin forms and fragments thereof. For example, in a Western blot assay a single type of antibody that recognizes all of the various actin fragments and the native actin itself may be employed, since the various fragments and native protein are pre-separated, e.g. by gel electrophoresis. However, where the various fragments and native protein are not separated prior to detection, e.g. in the competitive and sandwich assays described above, it is desirable to use a plurality of antibodies which are capable of specifically recognizing only a single actin species of interest, with substantially no cross-reactivity with other actin species or fragments that may be present in the sample.

In the subject methods, the sample or fractions thereof are at least assayed for the presence or absence of the low molecular actin fragments or species, and often times the native species as well, where the assay may be a direct assay for low molecular weight fragments or an indirect assay for low molecular weight fragments, as indicated above. In some embodiments, qualitative results are sufficient. Thus, one may be interested in identifying the presence or absence of the low molecular weight actin fragments as a marker for the chronic immune disease, e.g. in the diagnostic methods described above. Alternatively, one may be interested in making a qualitative determination of the ratio of the low molecular weight species to the native species. In many embodiments, the assays employed at least provide semi-quantitative detection of the various molecular weight actin species, and not just qualitative detection.

In assaying for low molecular weight actin fragments or species in the subject methods, one may look for: (a) the presence or absence of the low molecular weight fragments; (b) the pattern of the low molecular weight fragments and, optionally full length actin (where by pattern is meant the presence of each fragment and, optionally relative amount of each fragment); (c) the ratio of the amounts of the various low molecular weight species to each other and/or to the full length actin; and the like; (d) the relative amount of high molecular weight or native actin to all actin species in the sample; etc.

In many embodiments, based on the presence or absence of the various molecular weight actin species, and usually the semi-quantitative values obtained for each of the species of interest, the chronic immune disease activity in the subject from which the sample was derived is characterized. This broad category of embodiments includes those in which the low molecular weight actin species are directly assayed, e.g., those methods where: (a) the simple presence or absence of low molecular weight species is used to characterize the disease; (b) the ratio of low molecular weight species to high molecular weight species is used to characterize the disease; and (c) the pattern or amounts of two or more different low molecular weight species is used to characterize the disease; etc.

In yet other embodiments, e.g. those based on assays which indirectly determine the presence or absence of low molecular weight actin species, the relative amounts of the various actin species in the sample to each other, e.g., the relative amount of native or high molecular weight actin to the total amount of actin, i.e., native actin and fragment species thereof, in the sample is used to characterize the chronic immune disease activity in the subject.

Characterization of chronic immune disease activity according to the subject methods typically involves comparing the results obtained to a table or other source of predetermined values or reference values which provide information about the disease activity in the host, e.g. that positively or negatively correlate to the presence of the chronic immune disease, a particular stage of the chronic immune disease, and the like. For example, a table of values may be consulted in this step, where the table comprises representative values for the high and low molecular weight proteins as found in patients suffering from the chronic immune disease of interest. The values may be presented in numerical form, in picture form (e.g. as bands on a gel), and the like. By comparing the observed values with these reference values, e.g. by comparing a pattern of the actin species in the sample to a reference pattern or picture, characterization of the disease activity, e.g. confirmation of diagnosis, determination of disease state, etc., is readily made. In other embodiments, the ratio of two or more of the different species and/or full length actin is then compared to reference list of ratios to characterize the chronic immune disease activity.

As summarized above, the subject methods are methods of characterizing chronic immune disease activity in a host. The term characterizing is used broadly to refer to derivation of any type of information about the state of the chronic immune disease in the host. As such, the subject methods may be used to confirm an initial diagnosis of chronic immune disease, to determine the state of the disease in a patient known to have the chronic immune disease, to monitor the progression of the disease, to predict the occurrence of an attack, and the like. Where the subject invention is employed to confirm an initial diagnosis, a sample is obtained from subject suspected of having the chronic immune disease (where the subject may be identified as described supra). For example, the sample is assayed for the presence of the high and low molecular weight actin species, a ratio of the two species is derived and then compared to reference values, where the reference values correlate given ratios to the presence or absence of the chronic immune disease.

The subject methods are also employed to determine the stage of the chronic immune disease in the subject. In other words, the subject chronic immune disease activity characterization methods may be employed to determine whether the patient is in a remission stage, a chronic stage etc. For example, the subject methods may be employed to determine whether an MS patient is in the relapsing-remitting stage or in the chronic progressive stage of the disease. To determine the stage of the disease, the observed values for the one or more actin species, and ratios where desired, in the assayed sample are compared to reference values which are correlated to a particular stage of chronic immune disease, e.g. remitting relapsing or chronic progressive stage of MS.

In yet other embodiments, characterization of disease activity yields information concerning the disease progression in the patient, e.g. whether disease progression has accelerated or slowed. For example, the initial characterization date, i.e. the amount of high and low molecular forms in the patient derived sample, could be employed as a baseline value to evaluate subsequent testings, e.g. at some time following the initial testing, e.g. 3 months. If the amount of low molecular weight form decreases in subsequent testing, this indicates that the disease is not progressing. Alternatively, if the amount of low molecular weight form increases, this indicates that the disease is progressing in severity.

The characterization data obtained from the subject methods may also be used to determine whether a particular therapeutic regimen is having positive affects with respect to the progression of the disease. For example, at various time periods during the course of treatment, the subject methods may be performed to obtain a reading of the amount of high and low molecular weight forms of the actin species of interest. If the amount of the low molecular weight marker is increasing, this indicates that the treatment regimen is not having the desired effect. Alternatively, if the amount of the low molecular weight marker is decreasing, this indicates that the treatment regimen is working.

In yet other embodiments, the characterization data obtained from the subject methods is used to predict when a chronic immune disease attack, e.g. MS attack, may occur. In this embodiment, the characterization data is compared to reference values, where some of the reference values correlate to the occurrence of an attack.

Depending on the particular test protocol, the subject methods may further include one or more additional assays associated with the chronic immune disease of interest. For example, one may couple the subject methods with assays that look for the presence of low molecular weight proteins that exhibit RNase L activity, the ratio of high to low molecular weight proteins that exhibit RNase L activity, etc., as described in U.S. Pat. No. 5, 985,565 and U.S. patent application Ser. No. 09/300,814, the disclosures of which are herein incorporated by reference. Other representative assays of interest include biochemical assays capable of identifying MS activity in the subject, e.g. assays which detect the presence of oligoclonal bands in cerebral spinal fluid (CSF). A variety of such assays are known to those of skill in the art and may be employed in the subject methods. See e.g. Mehta et al., Electrophoresis. (Mar. 1988) 9(3): 126–8; Mehta, et al., J Clin Lab Immunol. (Jul. 1981) 6(1):17–22; Trbojevic-Cepe et al., Neurologija. (1989)38 (1): 11–21; Lasne et al., J Neurochem. (May 1981)36(5): 1872–4; Mehta et al., J Neurosci Methods. (Jun. 1986) 16(4):277–82.

Also provided by the subject invention are kits for use in carrying out the subject methods. The kits at least comprise reagents necessary for carrying out the actin species detection assays, where such kits may include: actin specific antibodies and/or immunoassay devices comprising the same; members of a signal producing system, such as antibodies, enzyme substrates, and the like; various buffers for use in carrying out the subject detection assays; and the like. The kits may further include one or more reagents necessary for preparation of the patient derived sample, such as heparin, Ficoll-Hypaque, lysing buffer, protease inhibitor, and the like, e.g. where the patient sample is PBMC derived, etc. In addition, the subject kits may further include one or more components employed in fractionation of the sample, such as an electrophoretic medium or precursors thereof, e.g. dried precursors of polacrylamide gels, one or more buffer mediums or components thereof, and the like. In most embodiments, the kits further include at least an information storage and presentation medium that contains reference data with which assay results may be compared in order to diagnose and/or characterize the chronic immune disease activity in the subject being assayed, i.e. reference data that includes various values of the high and low molecular weight actin species and relates these values to the presence or absence of chronic immune disease and/or the activity of the disease in the host. The information storage and presentation medium may be in any convenient form, such as a printed information on a package insert, an electronic file present on an electronic storage medium, e.g. a magnetic disk, CD-ROM, and the like. In yet other embodiments, the kits may include alternative means for obtaining reference data, e.g. a website for obtaining the reference data "on-line." The kits may further include means for obtaining the patient sample, e.g. a syringe. The subject kits further typically include instructions for carrying out the subject methods, where these instructions may be present on a package insert and/or the packaging of the kit. Finally, the kit may further include one or more reagents from an additional biochemical assay which is used to detect the presence of and/or characterize the chronic immune disease of interest. For example, where MS is the chronic immune disease of interest, the kits may further include one or more reagents from an assay designed to detect the presence of oligoclonal bands in CSF, e.g. immunoxification reagents (e.g. anti-IgG); labeling reagents, such as silver salts, and the like.

Also provided by the subject invention are assay methods for use in detecting the proteolytic activity of a sample with respect to actin and/or RNase L. In these assay methods of the subject invention, a subject sample, as described above, is contacted with a source of native actin and/or RNase L under conditions sufficient for actin and/or RNAse L protein cleavage products to be generated if the sample comprises the proteolytic activity of interest. Generally, contact is maintained for a period of time sufficient for a representative amount of cleavage products to be produced, where this incubation time typically ranges from about 5 to 120 minutes, usually from about 30 to 60 minutes. The source of RNase L and/or actin that may be used in these assays may be any convenient source. As such, the source may be a naturally occurring source, a recombinant source and the like.

Any convenient cleavage product detection format may be employed. Depending on the detection format employed, the source of RNase L and/or actin may or may not be labeled. For example, one convenient assay employs the use of substrate bound RNase L and/or actin, where the proteins are labeled, generally proximal to or at the end of the protein that is not attached, either directly or indirectly, to the substrate. The substrate bound protein is then contacted with the sample, as described above, and, following incubation, any cleavage products, e.g. low molecular weight actin or RNAse L cleavage produces, are detected. Non-labeled protocols may also be employed, e.g. antibody based (such as Western blot formats) as described supra.

Following detection of the cleavage products, the presence of, and generally amount of, cleavage products is related to the proteolytic activity of the sample, specifically the RNase L and/or actin proteolytic activity of the sample. In other words, the pattern of RNase L and/or actin cleavage products or proteins in the sample is related to the proteolytic characteristics or ability of the sample. For example, the presence of cleavage products indicates that the sample comprises the target proteolytic activity, while the amount of the cleavage products indicates the level of proteolytic activity.

The above assay for proteolytic activity in the sample may be employed in many applications. For example, the above proteolytic activity assay may be employed in addition to, or as a substitute for, the actin species detection assays in the above described methods of diagnosing and/or characterizing chronic immune disease activity.

Also provided are kits for use in practicing the subject proteolytic activity assays. The subject kits include, among other components, a source of RNase L and/or actin (e.g. source of full length actin and/or RNase L), where the source may be stably associated with the surface of a substrate and/or labeled, depending on the nature of the assay to be performed. Generally, the kits will also comprise a medium having reference values recorded thereon for use in interpreting the assay data and relating the data to the proteolytic activity in the sample.

The following examples are offered by way of illustration and not by way of limitation.

EXPERIMENTAL

I. Analysis and Quantification of Low and High Molecular Weight RNase L Protein Species as Compared to Low and High Molecular Weight Actin Species in Cell Extracts from CFS Patients, MS Patients and Healthy Controls Study subjects were 48 patients who had previously been diagnosed as fulfilling the diagnostic criteria for CFS, 22 patients who had previously been diagnosed as fulfilling the diagnostic criteria for MS and 37 healthy controls (non-CFS or MS subjects). Patients and controls were selected from medical practices in Overpelt and Brussels, Belgium. At the time of blood sampling, patient symptoms were evaluated and recorded.

A. Procedures

1. Extraction

Peripheral blood mononuclear cells (PBMCs) were separated from heparinized blood (30 mLs) by Ficoll-Hypaque density gradient centrifugation. Briefly, the heparinized blood was layered onto 20 mLs of Ficoll-Hypaque (Boyum, Scandinavian Journal of Clinical Laboratory Investigation, 97:1–109, 1968) at a density of 1.077 g/mL at 20° C. and centrifuged for 30 minutes at 500×g. The PBMC layer was removed and washed once with 5 volumes of phosphate buffered saline (PBS). The cells were then resuspended in 5 mLs of red blood cell lysing buffer (155 mM $NH_4Cl$, 10 mM $NaHCO_3$, 0.1 mM EDTA, pH 7.4), kept on ice for 5 minutes, then centrifuged for 5 minutes at 500×g. The resultant cell pellet was washed one time with 15 mLs of PBS and centrifuged for 5 minutes at 500×g. The resultant pellet must was then stored at less than −70C until the protein extraction procedure could be performed.

To extract the proteins from the cell pellet, the PBMCs were resuspended in a volume approximately 5–10 times the cell volume in the extract buffer (10 mM HEPES, pH 7.6, 90 mM KCl, 1.5 mM Mg(OAc)$_2$, 0.5% non-ionic detergent (such as Nonidet P-40 or Igepal CA-630, Sigma Chemical Corporation)). The extract buffer also contained a mixture of protease inhibitors to help stabilize the extract and impede the action of proteases (specifically those proteases liberated in the course of making the extracts), i.e. the MiniComplete protease inhibitor cocktail (Boehringer-Mannheim) which contains aprotinin, leupeptin, pefabloc-SC and EDTA.

The extraction procedure was performed at 2–4 degrees C., holding the cell pellet-extraction buffer in ice water or on wet ice for 5 minutes. The cell pellet-buffer mix was then vortexed at medium speed for 2 minutes at room temperature to ensure complete solubilization of the cell membranes. The cell pellet-buffer mix was then placed at 2–4C for an additional 5 minutes. The final step was to centrifuge the cell pellet-buffer mix at high speed in a microcentrifuge (16,000×g) for 2 minutes. The supernatant containing the proteins of interest was collected and the cell pellet is discarded. All cell extracts were stored at −70C until further analysis could be performed.

2. Quantification i. RNase L Quantification

Quantification of protein in the patient cell extracts was performed using a standard commercially available procedure of a modified Bradford method (Bio-Rad Laboratories). Analysis of LMW and HMW RNase L Proteins was performed using a radiolabeled 2'–5' A trimer and SDS-PAGE as described by the method of Charachon et al. (Biochemistry 29:2550–2556, 1990), the entire disclosure of which is incorporated herein by reference. Briefly, 2'–5' A trimer was radiolabeled by the ligation of $^{32}$P-pCp to the 3' end (method of Charachon). After removal of the 3' terminal phosphate by treatment with bacterial alkaline phosphatase, the 3' ribose residue of pC was oxidized with sodium metaperiodate (10 mM final concentration, pH 4.75) for one hour at 4° C. to form 2'5'A-$^{32}$pC-OX. This reaction mixture was subsequently equilibrated to pH 8.0 by the addition of NaOH. This oxidized molecule was used as the radiolabel in all subsequent reactions for RNase L protein analysis (referred to below as radiolabeled 2'5' A). The radiolabeled 2'5' A was incubated with 200 micrograms of cell extract at 2–4° C. for 15 minutes to allow the radiolabeled 2'5' A to interact with any 2'5'A-binding proteins present, such as RNase L (all species). The 2'5' A radiolabel was then covalently attached to all RNase L species by the addition of cyanoborohydride (20 mM in 100 mM phosphate buffer, pH 8.0); the cyanoborohydride reduces the oxidized ribose forming a covalent attachment to any amino groups nearby. The reduction reaction was allowed to occur for 20 minutes at room temperature. SDS-PAGE sample buffer, including a tracking dye, was added to the samples and all samples were incubated at 95×C for 5 minutes to reduce any disulfide bonds present.

The samples were then subjected to standard SDS-polyacrylamide gel electrophoresis using a 4 percent stacking gel and a 10 percent separating gel (Bisbal et al, European Journal of Biochemistry 179:595–602, 1989). The gel was electrophoresed until the tracking dye had migrated to the bottom of the gel. The gel was then dried and subjected to autoradiography. The autoradiographs were then analyzed by densitometry, and quantification of any and all RNase L species present was performed using specialized software (Quantity One; Bio-Rad Laboratories). The results are provided in Table 1, infra.

ii. Actin Quantification

Quantification of protein in the patient cell extracts was performed using a standard commercially available procedure of a modified Bradford method (Bio-Rad Laboratories). Analysis of actin and actin fragment proteins was performed using SDS-PAGE and Western blotting.

Briefly, the procedure used is as follows: 200 micrograms of protein extracted from the cytoplasm of PBMCs was mixed with 2×SDS-PAGE gel sample dye that included a tracking dye, and heated to 95° C. for five minutes to denature the proteins. The denatured samples were then subjected to standard SDS-PAGE using a four percent stacking gel and ten percent separating gel (Maniatis). Also included in the first lane of each gel was a molecular weight marker, pre-stained to be visible as it migrated during the course of electrophoresis (Bio-Rad Laboratories). The gel was electrophoresed until the tracking dye had migrated to the bottom of the gel.

The gel was then transferred to a PVDF membrane (Bio-Rad Laboratories) using a semi-dry transfer system (Amersham-Pharmacia Biotech). Transfer was performed at an average current of 0.8 milliamp per cm$^2$ of gel (or 100 mA for a standard 15 cm×8 cm gel) for two hours.

After transfer was complete (as determined by the visual agreement of the transfer of the color from the pre-stained molecular weight markers to the membrane), the membrane was allowed to dry thoroughly at room temperature for at least one hour.

Western blotting was performed using the following format: The membrane was first wet with a minimum volume of 100 percent methanol (according to the manufacturer's instruction). Then a solution of five percent non-fat dry milk (5% NFDM) was used to 'block' the membrane ('blocking buffer') to eliminate non-specific background binding of antibody. The membrane was 'blocked' for one hour with gentle shaking on an orbital shaker.

The blocking buffer was discarded and fresh blocking buffer was added in the amount of approximately 0.1 mL per cm$^2$ of membrane, to which was added the primary antibody (rabbit anti-actin; Sigma Corporation) at a 1:500 dilution according to the manufacturer's recommendations. The membrane was allowed to react with the primary antibody for one hour with gentle shaking on an orbital shaker. The primary antibody solution was then discarded and the membrane was washed three times with 25 mLs per wash of phosphate buffered saline (PBS, pH=7.4) plus 0.1% Tween 20 (polyoxyethylene sorbitan monolaurate; Sigma Corporation). Each wash was five minutes in length, with shaking, and the each time the solution was discarded.

Fresh blocking buffer was added in the amount of approximately 0.1 mL per cm$^2$ of membrane, to which was added the secondary antibody (goat anti-rabbit antibody, conjugated to horseradish peroxidase (GAR-HRP); Bio-Rad Laboratories) at a 1:2000 dilution according to the manufacturer's recommendations. The membrane was allowed to react with the secondary antibody for thirty minutes with gentle shaking on an orbital shaker. The secondary antibody solution was discarded and the membrane was washed three times with 25 mLs per wash of phosphate buffered saline (PBS, pH=7.4) plus 0.1% Tween 20. Each wash was five minutes in length, with shaking, and the each time the solution was discarded.

Color development was performed using the Opti4-CN kit (Bio-Rad Laboratories) according to the manufacturer's recommendations. Color development was allowed to proceed for 15 minutes and the membrane was then rinsed in copious changes of water and allowed to dry at room temperature. The results are shown in FIG. 1. The membrane was then analyzed by densitometry and quantification of actin and actin fragment proteins present was performed using specialized software (Quantity One; Bio-Rad Laboratories).

B. Analysis of Results

FIG. 1 represents a densitometric scan of a Western blot detecting actin protein and actin protein fragments. Native G-actin is clearly visible at 42 kDa as are the fragments (the 30 kDa fragment is indicated with an arrow).

In the data set forth in Table 1, a numerical value for both RNase L and actin protein ratios is calculated as the "ratio of the low molecular weight species to high molecular weight species, multiplied by a constant value of 10." In the case of RNase L, the relative amount of protein at an approximate molecular weight of 37 kDa was divided by the relative amount of native protein at 80 kDa (the 'RNase L protein ratio;' data not shown. See De Meirleir, et al., 2000, for reference). In the case of actin, the relative amount of protein at an approximate molecular weight of 30 kDa was divided by the relative amount of native protein at 42 kDa (the 'actin fragment ratio'). Data are organized by disease classification of the patient at the time of specimen collection (i.e., CFS, Healthy Control, and MS).

TABLE 1

Correlation Between RNaseL and Actin Values in CFS Patients, Controls, and MS Patients

| Specimen # | RNase L Value (LMW/HMW) * 10 | Actin Value (LMW/HMW) * 10 | Diagnosis |
|---|---|---|---|
| 1 | 2.3 | 1.9 | CFS |
| 2 | 6.5 | 2.2 | CFS |
| 3 | 2.9 | 5.6 | CFS |
| 4 | 5.8 | 5.8 | CFS |
| 5 | 3.8 | 3.8 | CFS |
| 6 | 25.0 | 5.8 | CFS |
| 7 | 8.3 | 4.4 | CFS |
| 8 | 5.5 | 6.0 | CFS |
| 9 | 3.7 | 5.0 | CFS |
| 10 | 5.6 | 7.8 | CFS |
| 11 | 5.9 | 9.2 | CFS |
| 12 | 5.0 | 6.6 | CFS |
| 13 | 8.2 | 8.3 | CFS |
| 14 | 4.3 | 5.2 | CFS |
| 15 | 2.7 | 5.3 | CFS |
| 16 | 4.2 | 4.0 | CFS |
| 17 | 8.4 | 7.5 | CFS |
| 18 | 32.9 | 6.3 | CFS |
| 19 | 4.6 | 5.9 | CFS |
| 20 | 27.9 | 7.0 | CFS |
| 21 | 9.4 | 6.0 | CFS |
| 22 | 7.6 | 5.1 | CFS |
| 23 | 2.5 | 3.0 | CFS |
| 24 | 3.3 | 5.3 | CFS |
| 25 | 53.3 | 8.2 | CFS |
| 26 | 2.6 | 7.0 | CFS |
| 27 | 10.4 | 5.1 | CFS |
| 28 | 2.2 | 4.9 | CFS |
| 29 | 7.7 | 8.2 | CFS |
| 30 | 3.7 | 4.5 | CFS |
| 31 | 2.0 | 8.0 | CFS |
| 32 | 6.0 | 4.9 | CFS |
| 33 | 14.6 | 4.6 | CFS |
| 34 | 3.0 | 5.8 | CFS |
| 35 | 10.0 | 9.5 | CFS |
| 36 | 2.5 | 2.7 | CFS |
| 37 | 4.0 | 5.5 | CFS |
| 38 | 18.0 | 9.7 | CFS |
| 39 | 20.0 | 5.0 | CFS |
| 40 | 32.3 | 8.3 | CFS |
| 41 | 14.4 | 5.5 | CFS |
| 42 | 22.8 | 8.5 | CFS |
| 43 | 4.7 | 4.3 | CFS |
| 44 | 8.6 | 6.7 | CFS |
| 45 | 12.5 | 5.4 | CFS |
| 46 | 2.5 | 5.2 | CFS |
| 47 | 6.1 | 8.7 | CFS |
| 48 | 7.5 | 9.1 | CFS |
| 49 | 1.2 | 1.2 | Control |
| 50 | 1.0 | 2.5 | Control |
| 51 | 1.0 | 3.3 | Control |
| 52 | 1.4 | 5.3 | Control |
| 53 | 1.3 | 3.1 | Control |
| 54 | 0.4 | 1.0 | Control |
| 55 | 1.7 | 3.6 | Control |
| 56 | 0.8 | 0.6 | Control |
| 57 | 1.6 | 0.3 | Control |
| 58 | 0.6 | 2.5 | Control |
| 59 | 0.7 | 0.7 | Control |
| 60 | 1.2 | 6.7 | Control |
| 61 | 0.9 | 3.2 | Control |
| 62 | 0.5 | 3.8 | Control |
| 63 | 0.2 | 2.4 | Control |
| 64 | 0.5 | 3.9 | Control |
| 65 | 1.0 | 0.3 | Control |
| 66 | 0.9 | 0.0 | Control |
| 67 | 1.5 | 0.1 | Control |
| 68 | 0.5 | 0.0 | Control |
| 69 | 1.2 | 0.5 | Control |
| 70 | 1.5 | 0.1 | Control |
| 71 | 0.7 | 4.9 | Control |
| 72 | 0.8 | 2.2 | Control |
| 73 | 1.3 | 3.3 | Control |
| 74 | 0.4 | 0.0 | Control |
| 75 | 0.3 | 0.0 | Control |
| 76 | 1.1 | 3.3 | Control |
| 77 | 0.2 | 0.1 | Control |
| 78 | 0.1 | 0.0 | Control |
| 79 | 0.1 | 0.0 | Control |
| 80 | 1.4 | 6.5 | Control |
| 81 | 0.1 | 0.0 | Control |
| 82 | 0.2 | 0.5 | Control |
| 83 | 1.3 | 3.8 | Control |
| 84 | 0.4 | 0.5 | Control |
| 85 | 0.9 | 2.1 | Control |
| 86 | 0.4 | 2.1 | MS |
| 87 | 6.3 | 4.8 | MS |
| 88 | 0.2 | 0.9 | MS |
| 89 | 0.1 | 0.5 | MS |
| 90 | 1.7 | 4.3 | MS |
| 91 | 0.9 | 2.8 | MS |
| 92 | 3.0 | 4.1 | MS |
| 93 | 0.8 | 1.4 | MS |
| 94 | 1.8 | 1.2 | MS |
| 95 | 4.2 | 3.8 | MS |
| 96 | 6.4 | 4.1 | MS |
| 97 | 2.2 | 1.3 | MS |
| 98 | 9.6 | 5.5 | MS |
| 99 | 0.7 | 1.5 | MS |
| 100 | 6.1 | 4.6 | MS |
| 101 | 9.7 | 3.8 | MS |
| 102 | 0.6 | 2.1 | MS |
| 103 | 0.2 | 0.1 | MS |
| 104 | 3.1 | 3.7 | MS |
| 105 | 4.5 | 3.6 | MS |
| 106 | 26.9 | 5.9 | MS |
| 107 | 3.5 | 3.8 | MS |

Figure 2:
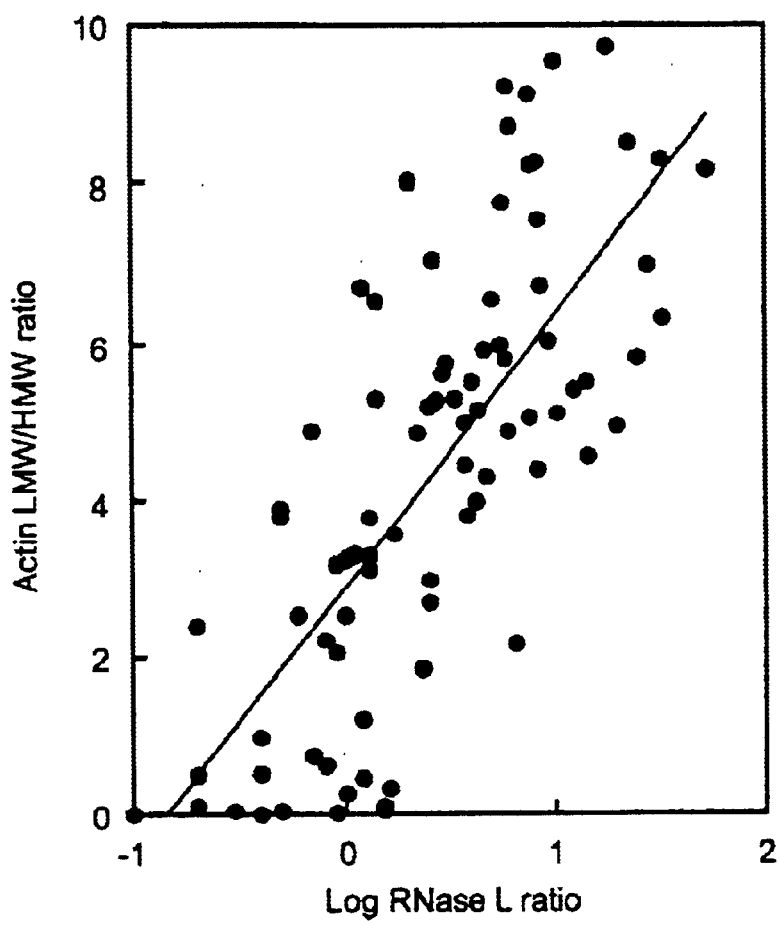
FIG. 2 provides a graphical representation of the correlation between the ratio of RNase L fragments [Log10 ((LMW/HMW)*10)] and the ratio of actin fragments [(LMW/HMW)*10] as assayed in PBMC Extracts. Data points in FIG. 2 are taken from Table 1, infra.

From the data in Table 1 above (and displayed graphically in FIG. 2), regression analysis was performed. The results are as follows:

1. In CFS patients, the ratio of RNase L [(LMW/HMW)*10] significantly corresponds to the ratio of actin [(LMW/HMW)*10]; $p<0.02$ 2. In healthy controls (Controls), the ratio of RNase L [(LMW/HMW)*10] significantly corresponds to the ratio of actin [(LMW/HMW)*10]; p<0.02
3. In MS patients, the ratio of RNase L [(LMW/HMW)*10] significantly corresponds to the ratio of actin [(LMW/HMW)*10]; p<0.001
4. In all samples assayed, the ratio of RNase L [(LMW/HMW)*10] significantly corresponds to the ratio of actin [(LMW/HMW)*10]; p<3×10$^{-17}$ Using a cut-off value of 2.0 for the RNase L ratio as the level of defining a patient with CFS (or MS) from a healthy control, the following results were obtained:

Of the 48 CFS patient samples included (RNase L ratio greater than 2.0), 45 had an actin fragment ratio greater than 3.0 (or 94 percent agreement)

Of the 37 healthy control samples included (RNase L ratio less than 2.0), 24 had an actin fragment ratio less than 3.0 (or 66 percent agreement)

Of the 22 MS patient samples included, 12/12 (or 100 percent) had an RNase L ratio greater than 2.0 and an actin ratio greater than 3.0. Of the MS samples having an RNase L ratio of less than 2.0, 11 had an actin fragment ratio of less than 3.0 (or 91 percent agreement)

II. Analysis and Quantification of the Relative Amount of High Molecular Weight RNase L Protein in PBMC as Compared to the Relative Amount of High Molecular Weight in Serum from CFS Patients, MS Patients and Healthy Controls A. Quantification Quantification of the relative amount of High Molecular Weight RNase L in PBMC extracts was performed as described above. Quantification of the relative amounts of native actin in serum was performed as described above, with the exception that instead of using PBMC extract, 250 micrograms of total serum protein was mixed with 2×SDS-PAGE gel sample dye. This mixture was then denatured and subjected to standard SDS-PAGE, transferred to PVDF membrane, and Western blotting performed exactly as describe in the text.

Quantification was performed by densitometry. Relative amount is defined as the amount of native or high molecular weight form present divided by the sum total of all forms of the protein present, i.e., native and all fragments thereof.

B. Results

The results are the above assay are provided in Table 2.

TABLE 2

Correlation Between RNaseL Ratio in PBMC Extracts, Relative Amount of Native RNase L Protein (80 kDa) in PBMC Extracts, and Relative Amount of Native Actin Protein (42 kDa) in Serum Samples of CFS Patients and Controls

| RNase L Ratio (LMW/HMW) * 10 in PBMC Extracts | Relative Amt. of Native RNase L Protein in PBMC Extracts | Relative Amt. of Native Actin Protein in Serum | Diagnosis |
|---|---|---|---|
| 0.2 | 98.3 | 79.9 | Control |
| 1.0 | 91.3 | 40.3 | Control |
| 1.7 | 85.2 | 33.1 | Control |
| 2.3 | 81.6 | 33.3 | CFS |
| 2.4 | 80.6 | 47.8 | CFS |
| 3.0 | 77.2 | 31.9 | CFS |
| 3.4 | 74.9 | 41.9 | CFS |
| 3.8 | 72.3 | 28.7 | CFS |
| 4.1 | 70.9 | 32.1 | CFS |
| 4.9 | 67.2 | 61.1 | CFS |
| 5.2 | 65.6 | 26.2 | CFS |
| 5.9 | 62.9 | 25.8 | CFS |
| 6.7 | 59.8 | 29.4 | CFS |
| 7.6 | 56.7 | 48.3 | CFS |
| 7.7 | 56.4 | 40.3 | CFS |
| 8.5 | 53.9 | 22.5 | CFS |
| 9.0 | 52.6 | 39.5 | CFS |
| 11.0 | 47.7 | 24.1 | CFS |
| 14.2 | 41.4 | 28.1 | CFS |
| 17.7 | 36.1 | 25.1 | CFS |
| 20.8 | 32.4 | 19.1 | CFS |

Relative amount=amount of native or high molecular weight form divide by the amount of all forms of the protein present, e.g., native and fragments thereof.

Figure 3:
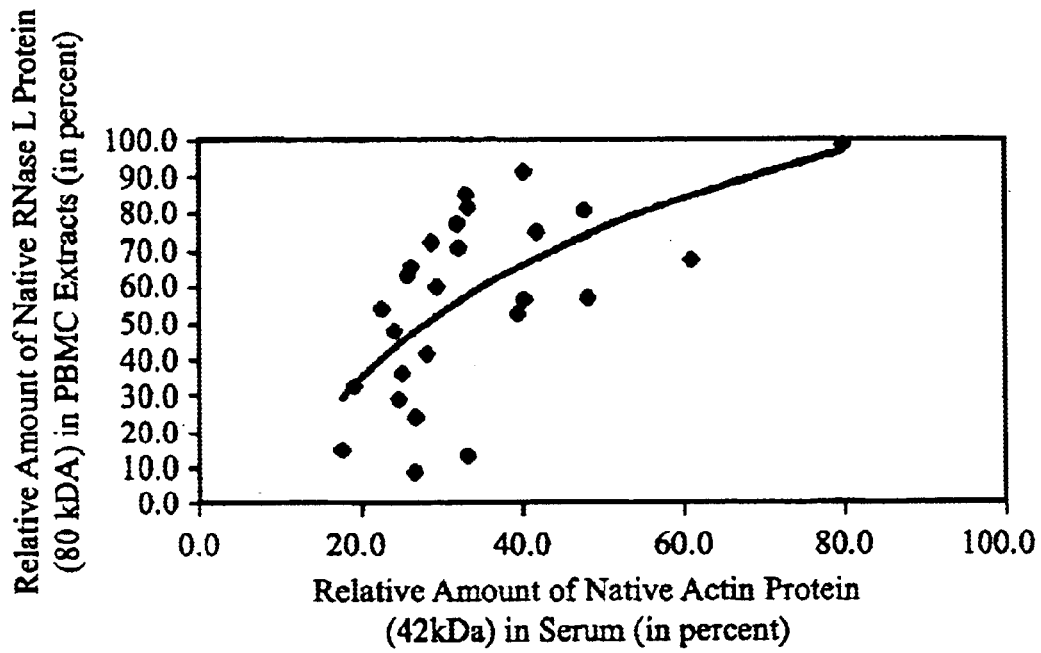
FIG. 3 provides a graphical representation of the correlation between the relative amount of native RNase L protein (80 kDa) in PBMC extracts and the relative amount of native actin protein (42 kDa) in serum. Data points are taken from Table 2, infra.

FIG. 3 provides a graphical representation of the above results.

The above results demonstrate that the serum relative amount of native actin can be used to characterize the chronic immune disease activity in a subject.

It is evident from the above results and discussion that relatively simple and rapid methods are provided for diagnosing and/or characterizing chronic immune disease (e.g. MS or CFS) activity in a subject are provided. With the subject methods, accurate diagnosis of the chronic immune disease condition, as well the identification of the stage and/or progression of the chronic immune disease condition, may be obtained. As such, the subject methods provide for more accurate diagnostic and/or treatment regimens. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for diagnosing whether a patient suffers from a chronic immune disease selected from the group consisting of Chronic Fatigue Syndrome (CFS) and Multiple Sclerosis (MS), said method comprising:
   (a) obtaining a sample from said patient; and
   (b) determining the relative amount of a low molecular weight actin protein fragment having a molecular weight of about 12 to about 37 kDa to native actin in said sample;
   wherein a ratio of greater than 3.0 of low molecular weight actin protein fragment to native actin as determined by the formula:
   (low molecular weight fragments/native actin)*10 is indicative of whether said patient suffers from said chronic immune disease selected from the group consisting of Chronic Fatigue Syndrome (CFS) and Multiple Sclerosis (MS).

2. The method according to claim 1, wherein said chronic immune disease is Chronic Fatigue syndrome (CFS).

3. The method according to claim 1, wherein said sample is a blood cell derived sample.

4. The method according to claim 1, wherein said sample is a peripheral blood mononuclear cell (PBMC) derived sample.

5. The method according to claim 1, wherein said chronic immune disease is Multiple Sclerosis (MS).

6. A method of diagnosing whether a patient suffers from a chronic immune disease selected from the group consisting of Chronic Fatigue Syndrome (CFS) and Multiple Sclerosis (MS), said method comprising:

(a) obtaining a sample from said patient; and (b) determining the relative amount of a low molecular weight actin protein fragment having a molecular weight of about 12 to about 37 kDa to native G actin in said sample;

wherein a ratio af greater than 3.0 of low molecular weight actin protein fragment to native actin as determined by the formula:

(low molecular weight fragments/native actin)*10 is indicative of whether said patient suffers from said chronic immune disease selected from the group consisting of Chronic Fatigue Syndrome (CFS) and Multiple Sclerosis (MS).

7. The method according to claim 6, wherein said chronic immune disease is CFS.

8. The method according to claim 6, wherein said sample is a blood derived sample.

9. The method according to claim 8, wherein said blood derived sample is derived from PBMCs.

10. The method according to claim 6, wherein said chronic immune disease is MS.

11. A method of diagnosing whether a patient suffers from a chronic immune disease selected from the group consisting of Chronic Fatigue Syndrome (CFS) and Multiple Sclerosis (MS), said method comprising:

(a) obtaining a sample from said patient; and (b) determining the relative amount of a low molecular weight actin protein fragment having a molecular weight of about 15 to about 37 kDa to native G actin in said sample;

wherein a ratio af greater than 3.0 of low molecular weight actin protein fragment to native actin as determined by the formula:

(low molecular weight fragments/native actin)*10 is indicative of whether said patient suffers from said chronic immune disease selected from the group consisting of Chronic Fatigue Syndrome (CFS) and Multiple Sclerosis (MS).

12. The method according to claim 11, wherein said chronic immune disease is CFS and MS.

13. The method according to claim 11, wherein said sample is a blood derived sample.

14. The method according to claim 11, wherein said blood derived sample is derived from PBMCs.

15. The method according to claim 11, wherein said chronic immune disease is MS.

* * * * *

UNITED STATES PATENT AND TRADEMARK OFFICE
CERTIFICATE OF CORRECTION

PATENT NO. : 6,824,988 B2
DATED : November 30, 2004
INVENTOR(S) : Roelens et al.

It is certified that error appears in the above-identified patent and that said Letters Patent is hereby corrected as shown below:

Column 22,
Line 17, after the word "ratio", correct the spelling of the word "af" to read -- of --.

Signed and Sealed this

Sixteenth Day of August, 2005

JON W. DUDAS
*Director of the United States Patent and Trademark Office*